United States Patent [19]

Sorbini

[11] 4,185,099
[45] Jan. 22, 1980

[54] HAIR AND SCALP TREATMENT WITH COMPOSITIONS CONTAINING CHENODEOXYCHOLIC OR URSODEOXYCHOLIC ACID

[75] Inventor: Paolo Sorbini, Milan, Italy

[73] Assignee: Also Laboratori S.a.S. di Dr.P. Sorbini & C, Milan, Italy

[21] Appl. No.: 868,563

[22] Filed: Jan. 10, 1978

[51] Int. Cl.² ............................................. A61K 31/56
[52] U.S. Cl. .................... 424/238; 424/DIG. 4; 424/106; 424/240; 424/264; 424/266; 424/317
[58] Field of Search ............... 424/106, 238, 240, 317, 424/DIG. 4, 264, 266, 70

[56] References Cited

U.S. PATENT DOCUMENTS

| 1,483,152 | 2/1924 | Altwegg | 424/106 |
| 1,901,960 | 3/1933 | Goss | 424/238 X |

FOREIGN PATENT DOCUMENTS

| 347126 | 4/1931 | United Kingdom | 424/238 |
| 348082 | 4/1931 | United Kingdom | 424/238 |

*Primary Examiner*—Joseph E. Evans
*Assistant Examiner*—Vera C. Clarke
*Attorney, Agent, or Firm*—Millen & White

[57] ABSTRACT

A cosmetic composition for treating the scalp comprises chenodeoxycholic acid or ursodeoxycholic acid and a cosmetically acceptable carrier.

7 Claims, No Drawings

HAIR AND SCALP TREATMENT WITH COMPOSITIONS CONTAINING CHENODEOXYCHOLIC OR URSODEOXYCHOLIC ACID

BACKGROUND OF THE INVENTION

This invention relates to chemical compositions adapted to be used, in different forms, for scalp treatment and for reduction of hair loss; more exactly it concerns chemical compositions comprising a particularly effective active substance. As is well known, in this field, various commercial formulations have been sold, generally in the form of locally applicable lotions, having a greater or lesser effectiveness. Recent studies in the field have shown that the use of synthetic non-ionic surface-active substances, such as those usually used in common detergent formulations, together with suitable carrier substances, produce a greater activity of the epithelium cells in the application zone, with attendant reduction of dandruff and beneficial effects against hair loss.

SUMMARY OF THE INVENTION

Starting from the above results, there has now been developed a composition exploiting the new and surprising features of an active substance that has proved to be perfectly effective for the desired purposes as well as perfectly tolerable by the users. According to this invention, the active substance, which is contained in said compositions, is a natural surface-active substance which exerts a preferential action on greases and specifically on cholesterol. In particular, said substance is in the form of a product obtained from the bile or of a derivative of the product obtained from the bile, such chenodeoxycholic acid, ursodeoxycholic acid, or a salt or derivative thereof.

DETAILED DISCUSSION

Since these active substances are obtained by known processes from a naturally secreted product i.e., the bile, they can be used in compositions of the stated type and in a general way for cosmetics, without any danger to the user of even local negative reactions, for instance allergic reactions, as may happen with synthetic products. As to the composition efficiency and in particular to the active substance efficiency, a particular and surprisingly great efficiency has been demonstrated by tests and experiences carried-out by Applicant. In fact, according to Applicant's studies, it is assumed that the epithelium degradation causing hair loss is mainly due, excluding pathologic cases, to the fact that a bunching of hormonal degradation products, and in particular, of cholesterol occurs around the cells. This hinders or even prevents the normal cell scission reproduction, which is not particularly hastened by an old organism. The stated bunching, above all of cholesterol, is prevented by said active substance, which shows a specific action against the same cholesterol and accordingly makes the substance more effective in freeing the cells from said bunchings, thereby putting the same in the best condition for their necessary reproduction. However, it is to be pointed-out that this invention is not bonded to a confirmation of the above hypotheses, as other favorable conditions could lead to the above results. The composition according to this invention may comprise the cited active substances in amounts from 0.6 to 1% by weight, together with additional substances having different functions, in particular adapted to make the active substance action easier and better. According to an advantageous embodiment of the invention, better results have been attained by a new and original combination of said active substances with a known substance adapted to stimulate cell proliferation, such as the retinoic acid, i.e., provitamin A, for instance in amounts from 0.01 to 0.25% by weight. Further substances may be advantageously included in said composition as for instance a moderately irritating substance which acts locally in order to improve the active substance's penetrability through the skin; carrier substances such as softening, moistening and similar substances; alcohol; perfumes, pH regulators, foam-producers and the like, according to the foreseen composition application method. In fact, depending upon the substances used in the composition, different products may be obtained, which can be used as lotions, elixirs, shampooing, before-shampooing and after-shampooing formulations and so on. Some non-limitative examples of possible compositions containing said active substance for scalp treatment follow:

EXAMPLES

| | |
|---|---|
| (1) Chenodeoxycholic acid | 0.66 g |
| Alcohol at 99° | 40.00 g |
| Propylene glycol | as necessary to reach 100 g |
| (2) Chenodeoxycholic acid | 1.00 g |
| Propylene glycol | 5.00 g |
| Polysorbitan stearate | 9.00 g |
| Nicotinic acid | 0.10 g |
| Urea | 1.00 g |
| Alcohol at 40° | |

Perfume and pH adjusters to attain values of about 6.

In the above composition, the propylene glycol acts as a thickening agent to improve the absorption by the skin, the polysorbitan stearate acts as a moistening substance and the nicotinic acid and urea act to obtain an improved and greater peripheral blood vessel feeding.

| | |
|---|---|
| (3) Chenodeoxycholic acid | 0.70 g |
| Nicotinamide | 0.20 g |
| Retinoic acid | 0.10 g |
| Vitamin $H_1$ | 0.10 g |
| Glycerol | 30.00 g |
| Propylene glycol | 30.00 g |
| Alcohol at 95° | as necessary to reach 100 g |
| (4) Chenodeoxycholic acid | 0.70 g |
| Nicotinamide | 0.20 g |
| Vitamin $H_1$ | 0.15 g |
| Thiolisone Complex 30 | 2.00 g |
| Glycerol | 25.00 g |
| Propylene glycol | 35.00 g |
| Alcohol at 95° | as necessary to reach 100 g |
| (5) Ursodeoxycholic acid | 0.90 g |
| Nicotinamide | 0.20 g |
| Retinoic acid | 0.10 g |
| Glycerol | 30.00 g |
| Propylene glycol | 30.00 g |
| Alcohol at 95° | as sufficient to reach 100 g |

The above compositions 3, 4 and 5 have been tested respectively on 7, 12 and 10 individuals of both sexes having a marked alopecia (hair loss), according to what follows:

| Composition No. 3 | | | |
|---|---|---|---|
| Exper. No. | Male Age | Female Age | Result |
| 1 | 26 years | — | ++ |
| 2 | 26 years | — | + |
| 3 | 32 years | — | +++ |
| 4 | 30 years | — | + |
| 5 | — | 25 years | — |
| 6 | — | 26 years | ++ |
| 7 | — | 22 years | ++ |

| Composition No. 4 | | | |
|---|---|---|---|
| Exper. No. | Male Age | Female Age | Result |
| 1 | 25 years | — | + |
| 2 | 28 years | — | ++ |
| 3 | 40 years | — | — |
| 4 | 36 years | — | + |
| 5 | 41 years | — | +++ |
| 6 | 32 years | — | + |
| 7 | 28 years | — | + |
| 8 | — | 28 years | — — |
| 9 | — | 23 years | + |
| 10 | — | 27 years | ++ |
| 11 | — | 32 years | ++ |
| 12 | — | 30 years | ++ |

| Composition No. 5 | | | |
|---|---|---|---|
| Exper. No. | Male Age | Female Age | Result |
| 1 | 40 years | — | — |
| 2 | 42 years | — | — |
| 3 | 40 years | — | ++ |
| 4 | 38 years | — | +++ |
| 5 | 51 years | — | + |
| 6 | 26 years | — | ++ |
| 7 | 28 years | — | ++ |
| 8 | — | 32 years | +++ |
| 9 | — | 30 years | ++ |
| 10 | — | 28 years | + |

+++ very positive
++ positive
+ satisfying
— — no modification
— poor or not detectable result The product has been used by application of 6–8 drops every evening on the treated scalp portions and a washing with a neutral shampooing every 3–4 days. The treatment has been carried-out over 5 months on the average, with a maximum of 7 months and a minimum of 3 months. The results may be summarized as follows: (1) Reduction of keratin immature flakes within a maximum term of 3 weeks. (2) Reduction of excessive hair loss within a maximum term of 3 months. (3) Hair growing in all cases wherein the involution process was not yet completed, within 4–5 treatment months. (4) Disappearance of itching and dandruff in all cases, one only excepted.

What is claimed is:

1. A cosmetic composition comprising an amount effective to treat dandruff of chenodeoxycholic acid, ursodeoxycholic acid, or a cosmetically acceptable salt or derivative thereof; a cosmetically acceptable carrier; and an amount of a cell proliferation stimulating substance which is effective to stimulate cell proliferation.

2. The composition of claim 1, wherein the effective amount of dandruff treating agent is 0.6 to 1% by weight.

3. The composition of claim 1, wherein the cell proliferation stimulating substance is retinoic acid.

4. The composition of claim 3, wherein the amount of retinoic acid is 0.10 to 0.25% by weight.

5. The composition of claim 4 which further comprises nicotinic acid, thereby increasing the penetrability through the skin, and alcohol.

6. The composition of claim 1, which has a pH value of about 6.

7. A method of lessening scalp dandruff comprising contacting the scalp with an amount of the composition of claim 1 effective to lessen scalp dandruff.

* * * * *